US00PP16320P2

(12) United States Plant Patent
Robertson

(10) Patent No.: US PP16,320 P2
(45) Date of Patent: Mar. 7, 2006

(54) ***CANNA* PLANT NAMED 'ROBTOYRED'**

(50) Latin Name: *Canna generalis*
Varietal Denomination: RobToyRed

(76) Inventor: Robert J. Robertson, P.O. Box 210, Grain Valley, MO (US) 64029

( * ) Notice: Subject to any disclaimer, the term of this patent is extended or adjusted under 35 U.S.C. 154(b) by 14 days.

(21) Appl. No.: 10/917,147

(22) Filed: Aug. 12, 2004

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Canna* plant named 'RobToyRed', characterized by its upright and compact plant habit; vigorous plant growth habit; non-persistent flowers; dark green-colored foliage; and flowers that are bright red in color.

2 Drawing Sheets

Botanical designation: *Canna generalis.*
Cultivar denomination: 'RobToyRed'.

BACKGROUND OF THE INVENTION

The present Invention relates to a new and distinct cultivar of *Canna* plant, botanically known as *Canna generalis*, and hereinafter referred to by the cultivar name RobToyRed.

The new *Canna* is a product of a planned breeding program conducted by the Inventor in Grain Valley, Mo. The objective of the breeding program is to create compact, fast-growing and freely-flowering *Cannas* with attractive flower coloration.

The new *Canna* originated from a cross-pollination made by the Inventor in August, 1997 of the *Canna* cultivar Roblibsca, disclosed in U.S. Plant Pat. No. 9,896, as the female, or seed, parent with the *Canna* cultivar Ambrosia, not patented, as the male, or pollen, parent. The new *Canna* was selected as a single plant from the resulting progeny of the above-stated cross-pollination by the Inventor in June, 1998 in a controlled environment in Grain Valley, Mo., on the basis of its compact growth habit and attractive flower coloration.

Asexual reproduction of the new cultivar by rhizome divisions in a controlled environment in Grain Valley, Mo., since September, 1998, has shown that the unique features of this new *Canna* are stable and reproduced true to type in successive generations.

SUMMARY OF THE INVENTION

Plants of the cultivar RobToyRed have not been observed under all possible environmental conditions. The phenotype may vary somewhat with variations in environment and culture such as temperature and light intensity without, however, any variance in genotype.

The following traits have been repeatedly observed and are determined to be the unique characteristics of 'RobToyRed'. These characteristics in combination distinguish 'RobToyRed' as a new and distinct *Canna* cultivar:

1. Upright and compact plant habit.
2. Vigorous plant growth habit.

3. Non-persistent flowers.
4. Dark green-colored foliage.
5. Flowers that are bright red in color.

Plants of the new *Canna* can be compared to plants of the female parent, the cultivar Roblibsca. In side-by-side comparisons conducted in Grain Valley, Mo., plants of the new *Canna* differed from plants of the cultivar Roblibsca in the following characteristics:

1. Plants of the new *Canna* were more compact than plants of the cultivar Roblibsca.
2. Leaves of plants of the new *Canna* were dark green in color whereas leaves of plants of the cultivar Roblibsca were burgundy in color.
3. Flowers of plants of the new *Canna* had broader petals than flowers of plants of the cultivar Roblibsca.

Plants of the new *Canna* can be compared to plants of the male parent, the cultivar Ambrosia. In side-by-side comparisons conducted in Grain Valley, Mo., plants of the new *Canna* differed from plants of the cultivar Ambrosia in the following characteristics:

1. Plants of the new *Canna* were more compact than plants of the cultivar Ambrosia.
2. Flowers of plants of the new *Canna* had bright red-colored petals whereas flowers of plants of the cultivar Ambrosia had pastel salmon-colored petals.

Plants of the new *Canna* can also be compared to plants of the cultivar President, not patented. In side-by-side comparisons conducted in Grain Valley, Mo., plants of the new *Canna* differed from plants of the cultivar President in the following characteristics:

1. Plants of the new *Canna* were much more compact than plants of the cultivar President.
2. Leaves of plants of the new *Canna* were lighter green in color than leaves of plants of the cultivar President.
3. Flowers of plants of the new *Canna* had deeper red-colored petals than flowers of plants of the cultivar President.
4. Flowers of plants of the new *Canna* were less persistent than flowers of plants of the cultivar President.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Canna*.

The photograph on the first sheet comprises a side perspective view of typical flowering plants of 'RobToyRed' grown in the landscape for about three years.

The photograph on the second sheet comprises a close-up view of typical flowers and a leaf of 'RobToyRed'.

DETAILED BOTANICAL DESCRIPTION

In the following description, color references are made to The Royal Horticultural Society Colour Chart, 1995 Edition, except where general terms of ordinary dictionary significance are used. Plants used for the description were grown in gallon containers after rooting and grown for about six months during the spring in a polyethylene-covered greenhouse in Grain Valley, Mo. During the production of the plants in the greenhouse, day temperature were about 24° C. and night temperatures were about 18° C. During the production of the plants, day temperatures were about 24° C. and night temperatures were about 18° C. Plants were flowered in Tolar, Tex. in an outdoor nursery during the summer about two months later.

Botanical classification: *Canna generalis* cultivar RobToyRed.

Parentage:

*Female, or seed, parent.*—*Canna generalis* cultivar Roblibsca, disclosed in U.S. Plant Pat. No. 9,896 .

*Male, or pollen parent.*—*Canna generalis* cultivar Ambrosia, not patented.

Propagation:

*Type.*—By rhizomes.

*Rhizome description.*—Tuberous; fleshy; covered with papery scales.

Plant description:

*Form.*—Upright and compact plant habit. Vigorous growth habit.

*Plant height.*—About 42 cm.

*Plant diameter.*—About 24 cm.

*Stem description.*—Length: About 41 cm. Diameter: About 1.6 cm. Internode length: About 3.6 cm. Strength: Strong. Texture: Smooth; glabrous. Color: 144A

*Foliage description.*—Arrangement: Opposite; simple. Length: About 28 cm. Width: About 18 cm. Shape: Ovate. Apex: Acute, mucronate. Base: Obtuse. Margin: Entire. Texture, upper and lower surfaces: Smooth; glabrous. Luster: Upper surface: Dull. Lower surface: Semi-glossy. Venation pattern: Pinnate. Color: Developing and fully expanded foliage, upper surface: More green than 147A. Developing and fully expanded foliage, lower surface: Close to 147A. Venation, upper surface: More green than 147B. Venation, lower surface: Lateral veins, close to 147A; midvein, close to 146C. Sheathing petioles: Length: About 9.3 cm. Diameter: About 2.75 cm. Texture, upper and lower surfaces: Smooth; glabrous. Color, upper surface: Close to 146D. Color, lower surface: Close to 146C.

Flower description:

*Flower type and habit.*—Single flowers arranged on terminal racemes; several racemes per plant.

*Natural flowering season.*—Throughout the summer in Missouri.

*Flower longevity on the plant.*—About seven to ten days.

*Fragrance.*—None detected.

*Flowers.*—Form: Salverform. Diameter: About 8 cm. Height: About 6.8 cm.

*Flower buds.*—Length: About 3.75 cm. Diameter: About 6 mm. Shape: Elongate, linear. Color: Close to 182A.

*Petals.*—Arrangement: About four in a single whorl, fused at the base. Length: About 7.4 cm. Width: About 4.3 cm. Shape: Spatulate. Apex: Rounded. Margin: Entire; slightly undulate. Texture, upper and lower surfaces: Smooth, velvety. Color: When opening, upper and lower surfaces: Close to 45A. Fully opened, upper and lower surfaces: Close to 45A.

*Sepals.*—Arrangement: About four in a single whorl. Length: About 4.3 cm. Width: About 1.5 cm. Apex: Acute. Texture, upper and lower surfaces: Waxy, smooth. Color, upper surface: 45A overlain with close to 9A. Color, lower surface: Close to 45A.

*Peduncles.*—Length: About 6 mm. Diameter: About 6 mm. Angle: About 40° from vertical. Strength: Strong. Texture: Smooth; glabrous. Color: Close to 187A.

*Bracts.*—Arrangement: Each inflorescence subtended by a bract. Length: About 5.7 cm. Width: About 3.2 cm. Texture, upper and lower surfaces: Waxy, smooth. Color, upper surface: Close to 194A. Color, lower surface: Close to 183A.

*Reproductive organs.*—Stamenoids: Quantity: About two, petal-like. Length: About 4.6 cm to 5.5 cm. Width: About 5 mm to 12 mm. Anther shape: Oblong, fused to stamenoids. Anther length: About 1.4 cm. Anther color: 9A. Pollen amount: Moderate. Pollen color: Close to 5D.

*Pistils.*—Quantity: One per flower. Pistil length: About 4.5 cm. Stigma shape: Tapering. Stigma color: Close to 5D. Style color: Close to 45A.

*Seed/fruit.*—Seed and fruit development has not been observed.

Disease/pest resistance: Plants of the new *Canna* have not been observed to be resistant to pathogens and pests common to *Canna* .

Weather tolerance: Plants of the new *Canna* have been observed to be very tolerant to rain and wind.

Temperature tolerance: Plants of the new *Canna* have been observed to be tolerant to temperatures ranging from 4 to 38° C.

It is claimed:

1. A new and distinct cultivar of *Canna* plant named 'RobToyRed', as illustrated and described.

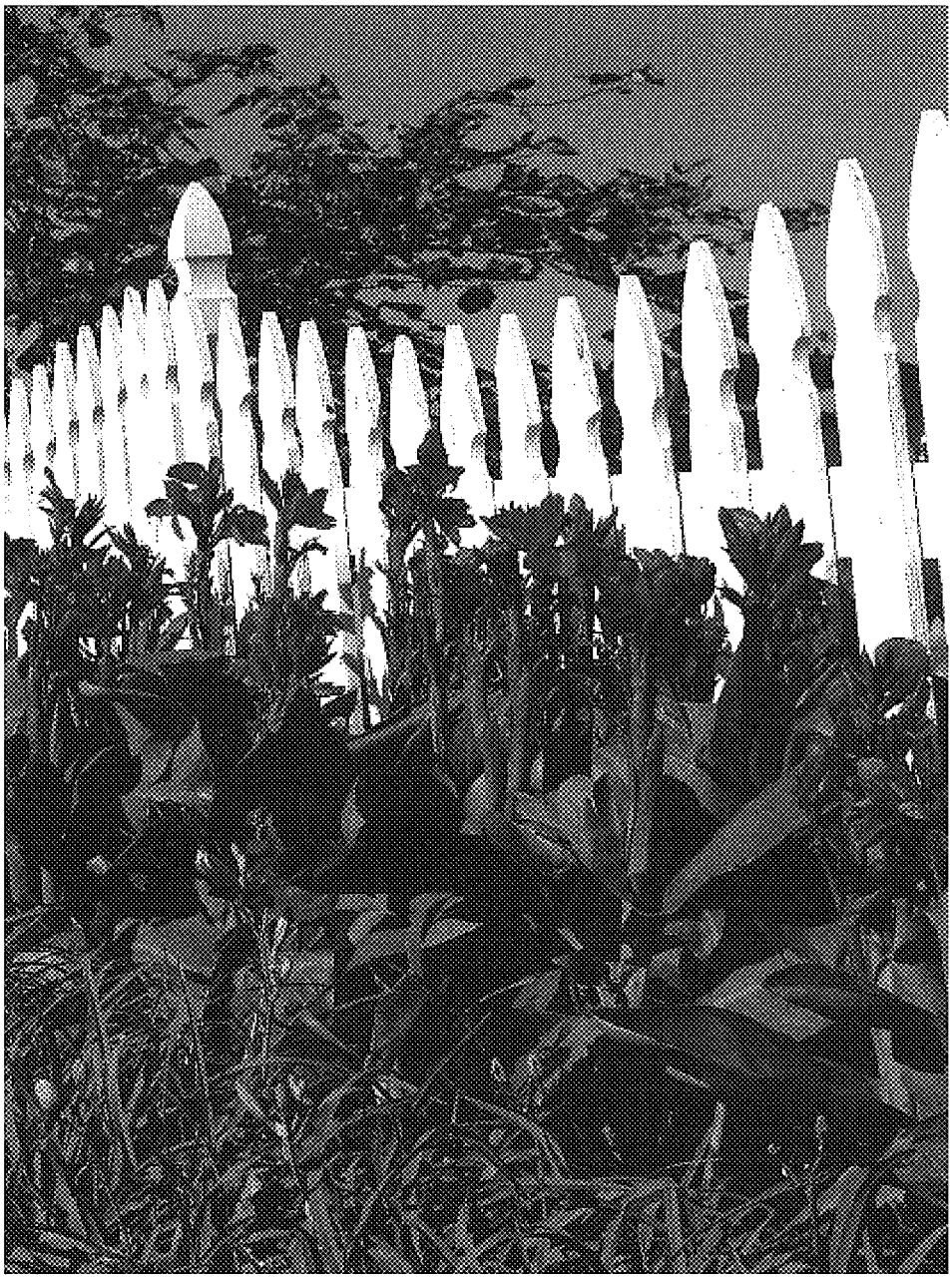

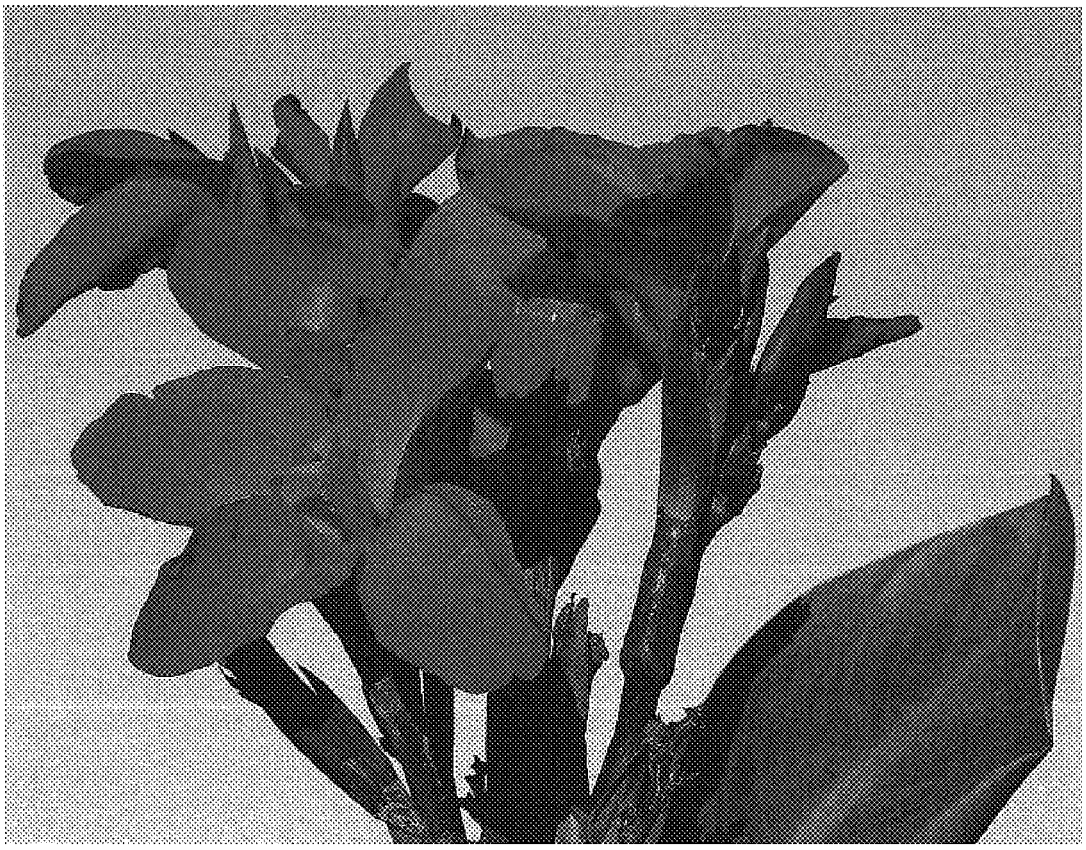

* * * * *